United States Patent [19]
Sauer et al.

[11] Patent Number: 5,544,186
[45] Date of Patent: Aug. 6, 1996

[54] GAS LASER FOR EMITTING LIGHT MODULATED AT TWO DIFFERENT WAVELENGTHS AND AN ARRANGEMENT INCORPORATING THE GAS LASER TO DETECT A GASEOUS SUBSTANCE

[75] Inventors: Ralf-Roland Sauer, Hüttlingen; Wolfgang Rupp, Aalen; Alexander Hinz, Königsbronn, all of Germany

[73] Assignee: Carl-Zeiss-Stiftung, Heidenheim-Brenz, Germany

[21] Appl. No.: 378,017

[22] Filed: Jan. 25, 1995

[30] Foreign Application Priority Data

Jan. 25, 1994 [DE] Germany ................. 44 02 054.6

[51] Int. Cl.⁶ .................................................. H01S 3/00
[52] U.S. Cl. ............................ 372/33; 372/23; 372/28; 372/98; 372/102; 372/20; 372/64
[58] Field of Search ..................... 372/64, 102, 98, 372/92, 20, 108, 99, 28, 33, 23, 26

[56] References Cited

U.S. PATENT DOCUMENTS

| | | |
|---|---|---|
| 4,471,220 | 9/1984 | Perry et al. . |
| 4,789,989 | 12/1988 | Stern et al. ................. 372/6 |
| 5,002,391 | 3/1991 | Wolfrum et al. . |
| 5,373,525 | 12/1994 | Nowack et al. ............. 372/64 |

FOREIGN PATENT DOCUMENTS

| | | |
|---|---|---|
| 0196856 | 10/1986 | European Pat. Off. . |
| 2127537 | 4/1984 | United Kingdom . |

OTHER PUBLICATIONS

"Carbon dioxide laser monitor for $NH_3$ in flue gas" by A. Stein et al, Applied Optics, vol. 22, No. 21, 1 Nov. 1983, pp. 3378–3381.

"Frequency–switching waveguide $CO_2$ laser for atmospheric pollution monitoring" by A. Gerasimchuk et al, Sov. J. Quantum Electron, 12(1), published by the American Institute of Physics, Jan. 1982, pp. 110–113.

"Frequency–switching waveguide $CO_2$ laser for atmospheric pollution monitoring" by A. Gerasimchuk et al, Sov. J. Quantum Electron, vol. 12, No. 1, Jan. 1982, pp. 110 to 112.

"Alternate Intensity Modulation of a Dual–Wavelength He–Ne Laser for Differential Absorption Measurements" by K. Uehara, Applied Physics, vol. 38, (1985), pp. 37 to 40.

*Primary Examiner*—Leon Scott, Jr.
*Attorney, Agent, or Firm*—Walter Ottesen

[57] ABSTRACT

A gas laser 1 such as a $^{13}CO_2$-laser emits at two different wavelengths ($\lambda_1$, $\lambda_2$) with a sine-shaped adjustment of a resonator mirror or a grating 13 such as a Littrow grating. The gas laser emits radiation at the two desired wavelengths ($\lambda_1$, $\lambda_2$) in two mutually adjacent intervals of the resonator length L because of a suitable dimensioning of the grating 13 with respect to grating structure and angle position, the outcoupling factor of the outcoupling mirror 12, the resonator length L and the composition of the gas of the laser. The laser emission is inhibited at the crossover between the two intervals and the sine-shaped modulation (for example with a piezo element) of the resonator length L is essentially symmetrical about this crossover. The invention is also directed to an arrangement for detecting a substance such as $NH_3$ in a flue gas. This arrangement includes a two wavelengths laser light source 1, a modulation unit 14 and a reference detection unit D1; a transmission optic 2; a measuring path 3 which contains the substance to be detected; a receiving optic 4 and a measuring detector D2. An evaluation apparatus 5 is also provided which determines the ratio of the light absorption in the measuring path 3 at the two wavelengths ($\lambda_1$, $\lambda_2$) and determines therefrom the concentration of the substance to be detected in the measuring path 3.

18 Claims, 4 Drawing Sheets

GAS LASER FOR EMITTING LIGHT MODULATED AT TWO DIFFERENT WAVELENGTHS AND AN ARRANGEMENT INCORPORATING THE GAS LASER TO DETECT A GASEOUS SUBSTANCE

FIELD OF THE INVENTION

The invention relates to a gas laser which emits light modulated at two different wavelengths by means of a sinusoidal displacement of a resonator mirror or a grating. The invention also relates to an arrangement incorporating the gas laser. This arrangement detects substances by different absorption of light of two wavelengths.

BACKGROUND OF THE INVENTION

European patent publication 0,196,856 discloses a laser for detecting a gas which operates at two emission wavelengths and is modulated by sinusoidal oscillations of a piezoelectrically-driven resonator mirror. The laser here is an IR—He—Ne laser having a methane cell. The modulation takes place at 1 kHz in such a manner that the sum of the intensities at both wavelengths together remains substantially constant. Nothing further is provided as to detection in this publication.

The detection of ammonia with a two-wavelength $CO_2$ laser is described in a paper of A. G. Gerasimchuk et al entitled "Frequency-Switching Waveguide $CO_2$ Laser for Atmospheric Pollution Monitoring" published in Sov. J. Quantum Electron 12 (1), January 1982, pages 110 to 112. The wavelength modulation takes place utilizing square wave control pulses via a piezoelectrically-driven mirror. A synchronous detector is provided.

The detection of $NH_3$ in flue gas from an industrial furnace utilizing two wavelengths of isotopically-selected $^{13}CO_2$ lasers is described in a paper of A. Stein et al entitled "Carbon Dioxide Laser Monitor for $NH_3$ in Flue Gas", Applied Optics, Volume 22, No. 21 (November 1983), pages 3378 to 3381 (see also U.S. Pat. Nos. 4,471,220 and 5,002,391). The paper of A. Stein et al and U.S. Pat. No. 4,471,220 disclose the use of two separate lasers for the two wavelengths and two mechanical choppers. U.S. Pat. No. 5,002,391 discloses a single laser having a mirror or grating which is shifted piezoelectrically with square wave pulses in order to alternately generate one of the two wavelengths. A synchronized mechanical chopper effects a blanking after each pulse pair at both wavelengths. Pyroelectric detectors and sample-and-hold circuits are utilized for detection.

British patent publication 2,127,537 discloses a gas detector having a laser which is preferably a $CO_2$ laser without a grating. The laser can emit by means of a piezoelectrically displaced resonator mirror at different wavelengths. The following are mounted in the measurement beam path: a mechanical chopper, a cooled photodetector and a phase-sensitive detector circuit. A reference cell having a pyroelectric detector is required.

SUMMARY OF THE INVENTION

The invention relates to a gas laser which is suitable as a light source in the detection beam path for detecting substances utilizing two wavelengths with different absorptions. It is another object of the invention to provide such a gas laser which can make the above detection without external circuit means, such as a chopper, in the detection beam path. It is still another object of the invention to provide such a gas laser which has a simple and robust assembly and a signal characteristic which can be easily processed electronically. It is still another object of the invention to provide a total system for the laser detection of a substance wherein the above laser characteristics are optimally utilized.

The use of such a gas laser in an arrangement for detecting a substance imparts the desired advantages to such an arrangement. This is especially the case for detecting trace gases in a gas and especially for detecting ammonia in flue gas.

The arrangement according to the invention utilizes the gas laser of the invention. Advantageous embodiments include providing a reflector in the open measuring path; a reference path having a cell for calibration purposes; an arrangement of a measuring path in a flue gas channel and the detection of $NH_3$; and means for adapting the laser power to the substance concentration or to the absorbing and scattering action of dust, smoke and other background disturbances thereby increasing the sensor dynamic. Such background disturbances can, for example, be dirt on or degradation of the windows (25,44) and/or mirror 41 (see FIG. 5). The means referred to above are, for example, attenuation filters which can be exchanged or pivoted into the beam path.

According to another embodiment of the invention, an arrangement is provided which operates without a chopper or a third detector for passing a reference beam through a calibrated cell. The complexity of the apparatus is thereby significantly reduced and the operational reliability is increased. An MCT detector is preferred as a measuring detector. The preferred configuration of the evaluation apparatus includes AC coupling of the reference detector and of the measuring detector, an amplifier circuit and an integration unit as well as an analog-to-digital converter and a programmable computer.

With respect to the foregoing, it is preferred that the integration unit integrates the signal received by the detector in each case over a substantial part of the time interval wherein the gas laser emits at one of the two wavelengths. In this way, a work signal of very low noise can be obtained very quickly. This is made possible primarily by means of the sinewave modulation which provides signal traces of low noise. The sensor dynamic can be increased with a favorable configuration of the other electronic circuit components. For this purpose, the amplification circuit can be automatically adjusted with respect to its amplification factor in dependence upon the signal of the measuring detector, for example, by factors of 10, 100 and 1,000.

Simply by means of a suitable programming of the computer is it possible at the same time to determine the flue gas density in the exhaust gas. This is determined from the transmission at the reference wavelength $\lambda_2$ which is not influenced by ammonia.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
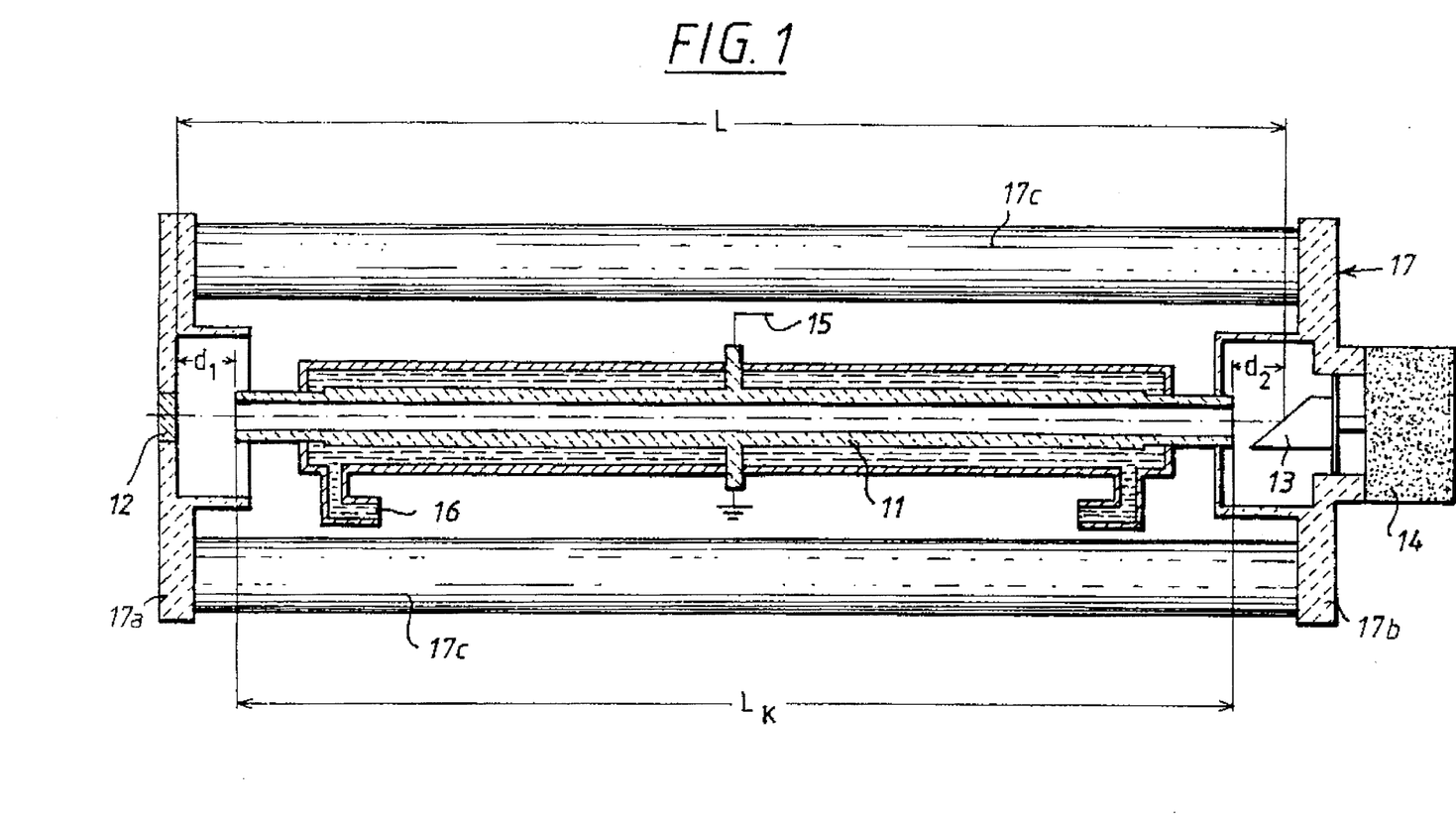
FIG. 1 is a schematic showing the assembly of an embodiment of the laser according to the invention.

The $CO_2$ laser 1 of FIG. 1 includes components known per se. The laser resonator includes a ceramic waveguide 11 having a length $L_k$, an out-coupling mirror 12 at a spacing $d_1$ and a grating 13 at a spacing $d_2$. The length L of the resonator can be adjusted with a piezoelectric actuating member 14. Excitation is via an HF line 15 and water cooling 16 is provided. The entire assembly is mounted in a stable housing 17. The housing 17 of the laser includes end pieces (17a, 17b) and rods 17c which can, for example, be made of ceramic or other dimensionally stable material such as invar or zerodur.

What is essential to the invention is the selection, dimensioning and control of the above-mentioned components. The wavelength selection of the desired wavelengths (here $\lambda_1=10.800$ μm and $\lambda_2=10.784$ μm) is determined by the grating 13 in a Littrow configuration. The grating 13 is so configured essentially with respect to the number of grating lines and therefore the resolution so that only the two desired spectral lines ($\lambda_1$, $\lambda_2$) can build up (optimal line density is approximately 150 lines/mm, Littrow angle 54.1°, reflection efficiency in the first order (that is, for autocollimation) is approximately 98%).

The ceramic waveguide 11 has a quadratic cross section which affords manufacturing advantages when compared to cross sections which are round. The ceramic waveguide 11 has an inner edge length of approximately 2 mm and a length $L_k=218$ mm. This inner edge length is the edge length of the gas containing opening of the rectangular ceramic tube. The entire length of the resonator ($L=d_1+L_k+d_2$) is decisive for optimal operation. If both lines have the frequencies $f_1$ and $f_2$, then with the following conditions, the two lines can build up simultaneously:

$$f_1-f_2=N\cdot FSR$$

wherein:

N=an integer (difference in the number of half waves $\lambda/2$ of lines 1 and 2).

FSR=free spectral range: c/2L (c=light velocity, L=resonator length).

A $CO_2$ laser having the isotope $^{13}C$ is used for detecting ammonia ($NH_3$). This laser has the following lines of the isotope $^{13}C$:

R(16), $\lambda_1=10.800$ μm: $f_1=27758500.36$ MHz and

R(18), $\lambda_2=10.784$ μm: $f_2=27799764.18$ MHz.

With respect to the above, reference can be made to U.S. Pat. No. 5,002,391 which is directed to a system for detecting $NH_3$.

In this way, for N=1, a total length of 3.63 mm results, that is, identical conditions are present at each 3.63 mm, for example:

(1) L = 3.63 mm;
672 halfwaves $\lambda_1$ } simultaneous emission of
673 halfwaves $\lambda_2$ } $\lambda_1$ and $\lambda_2$
(2)
(i) L = (3.63 + 3.63/2) mm = 5.443 mm: (exactly 5.4432 mm):
1008.0 halfwaves $\lambda_1$ } emission only of
1009.5 halfwaves $\lambda_2$ } $\lambda_1$
(ii) L = 5.4432 mm + ($\lambda/4$ = 2.7 μm) = 5.4459 mm:
1008.5 halfwaves $\lambda_1$ } emission only of
1010 halfwaves $\lambda_2$ } $\lambda_2$
(3) L = 2 × 3.63 mm = 7.26 mm:
1344 halfwaves $\lambda_1$ } simultaneous emission of
1346 halfwaves $\lambda_2$ } $\lambda_1$ and $\lambda_2$ A time-dependent sequence of laser emissions at $\lambda_1$ and $\lambda_2$ is obtained by selecting the resonator length L in a manner similar to case (2), that is:

$$L=(n+\tfrac{1}{2})\times 3.63 \text{ mm}.$$

Figure 2:
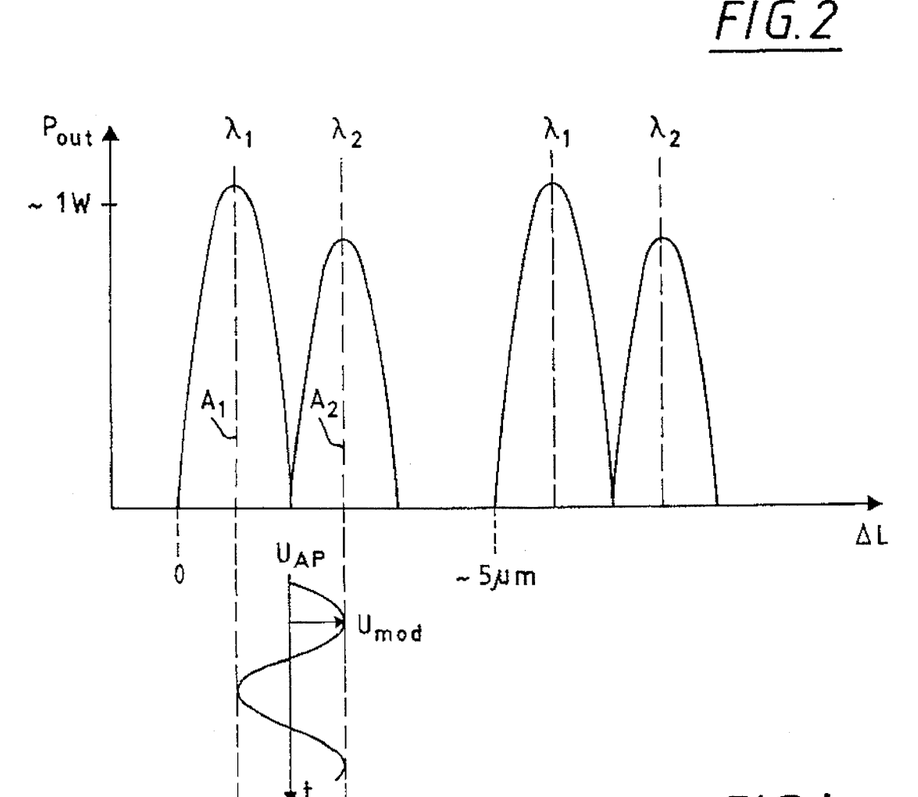
FIG. 2 is a graph showing the signature of the laser of the invention.

In this case, a maximum separation of the two lines ($\lambda_1$, $\lambda_2$) results in dependence upon resonator length L (see FIG. 2). In the concrete embodiment, the resonator length L is adjusted to 248.7+0.2 mm (68.5.3.63 mm).

The alternating emission is achieved (see cases (2i), (2ii)) by sinusoidal changes of the resonator length L in the region of one-quarter wavelength (approximately 27 μm) with the piezoelectric positioning element 14 which linearly displaces the grating 13 in the direction of the optical axis of the laser 1.

The radius of curvature $r_{12}$ of the out-couple mirror 12 and the reflectivity $R_{12}$ are given as: $r_{12}=500$ mm, $R_{12}=90\%$. The reflectivity is determined by the following: the amplification of the laser medium (that is, by the gas composition, gas pressure, et cetera), the loss within the resonator and the pump capacity. The laser gas is a conventional mixture of He, $^{13}CO_2$ as laser active gas, N and Xe. The gas pressure amounts to approximately 120 mbar and the in-coupled HF power lies in the order of magnitude 40 W to 70 W. Losses internal to the resonator are primarily determined by the Littrow grating 13 (reflection, scattering, absorption) and the waveguide 11 and amount to approximately 3% to 5%. The laser output power at $\lambda_1=10.800$ μm or $\lambda_1=10.784$ μm is approximately 1.2 W.

FIG. 2 shows a typical signature of the $^{11}CO_2$ laser, that is, the output power $P_{mod}$ is a function of the change $\Delta L$ of the resonator length L.

A bias voltage $U_{AP}$ is applied to the piezoelectric positioning element 14 for operation so that the signature is at a minimum. In this point, a sinusoidal modulation $U_{mod}$ is impressed whereby the voltage at the piezoelectric positioning element is varied upwardly and downwardly and the laser 1 is driven into the maximum of the power curve of $\lambda_1$ and thereafter into the maximum of the power curve of $\lambda_2$. Deviations from the maximum are permissible. The bias voltage $U_{AP}$ is actively stabilized to the operating point by the programmable computer 57. A signal sequence, which corresponds to the signature form, results in correspondence to the modulation frequency.

Figure 3:
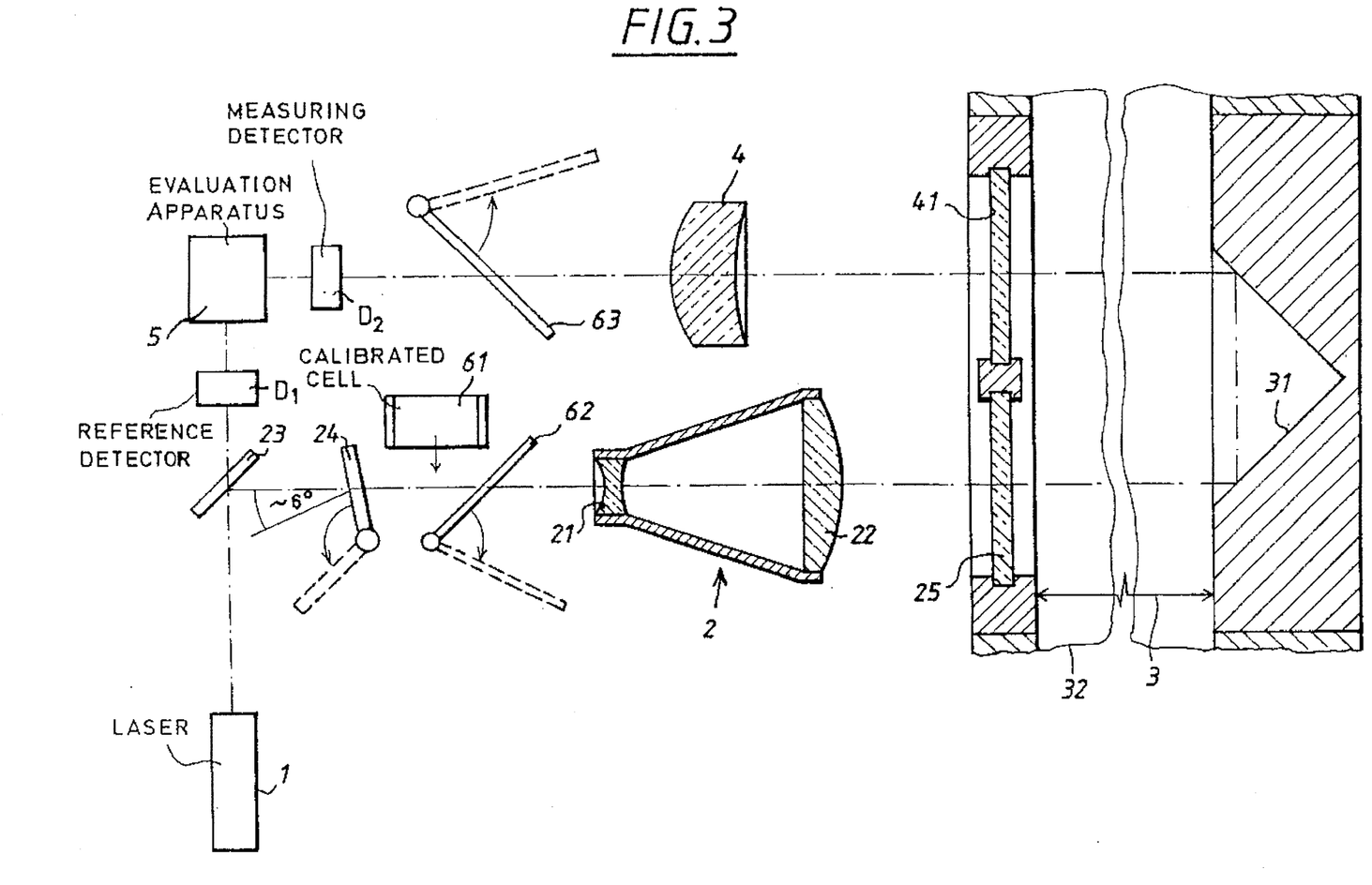
FIG. 3 is a schematic of the optical configuration of an arrangement for detecting substances.

FIG. 3 shows the optical configuration of an $NH_3$ detector for flue gas in a flue-gas channel 32 (an open effluent dust). Approximately 1% of the power of the laser beam emitted by the laser 1 is supplied at beam splitter 23 to a reference detector D1, which is configured as a pyroelectric detector, for detecting the instantaneous laser power. The transmission optic 2 is a telescope having two lenses (21 and 22) for beam widening. The laser beam enters the flue-gas channel 32 through the end window 25 and passes through the measuring path 3 in the channel. A retroreflector 31 deflects the beam to the end window 41.

The measuring path has a length of approximately 1 m to 20 m and can be folded several times in the flue-gas channel 32 (see U.S. Pat. No. 5,002,391); or, the measuring path can have one reflector or no reflectors. The laser beam is specifically weakened in the measuring path and reaches the measuring detector D2 via the receiving optics in the form of a collector lens 4. The measuring detector D1 is an MCT detector. MCT detectors are special photoresistors made of mercury-cadmium-telluride. These MCT detectors can be thermoelectrically cooled to approximately 60° C. and have very short response times.

The signals of reference detector D1 and measuring detector D2 are supplied to the evaluation apparatus 5. For measuring very low background concentrations, the laser beam can be attenuated, for example, to one percent by means of a filter 24 which can be pivoted in to protect the detectors. For calibration purposes, the laser radiation can bypass the measuring path 3 and be directed directly onto the measuring detector D2 via gold mirrors (62, 63) which can be introduced into the radiation path. In this way, the detections made with detectors D1 and D2 can be balanced (zero measurement). In addition, a calibrated cell 61 having a known $NH_3$ content can be introduced to calibrate the absorption strength at two wavelengths $\lambda_1$ and $\lambda_2$ (reference measurement).

Figure 4:
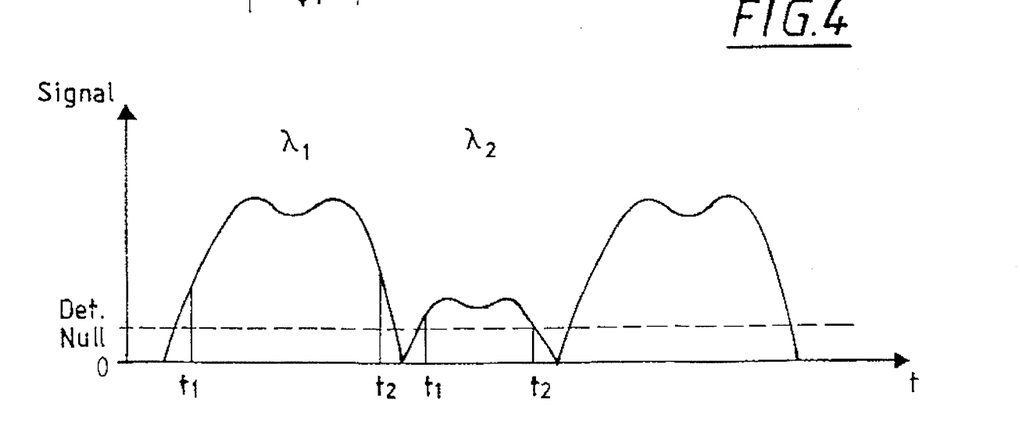
FIG. 4 is a graph showing the signal of the measuring detector of the arrangement of FIG. 3; and, FIG. 5 is a block diagram representation of an embodiment of an arrangement according to the invention for detecting substances.

FIG. 4 shows the measuring signal occurring at the measuring detector. Because of the signature described in FIG. 2, the zero point is reached each time that there is a transition between laser emission at $\lambda_1$ to $\lambda_2$ and vice versa. The time point $t_1$ and $t_2$ define respective limits of the integration time which leave only narrow time intervals around the wavelength-switchover unused for signal sampling. The valleys in the center of the signal traces occur when the modulation voltage $U_{mod}$ somewhat exceeds the maximum of the signature (FIG. 2). The drawings show that the detectors (D1, D2) have a zero position shifted by an offset because of an AC coupling. The offset control (53, 53R) is provided for this reason as also described below.

Figure 5:
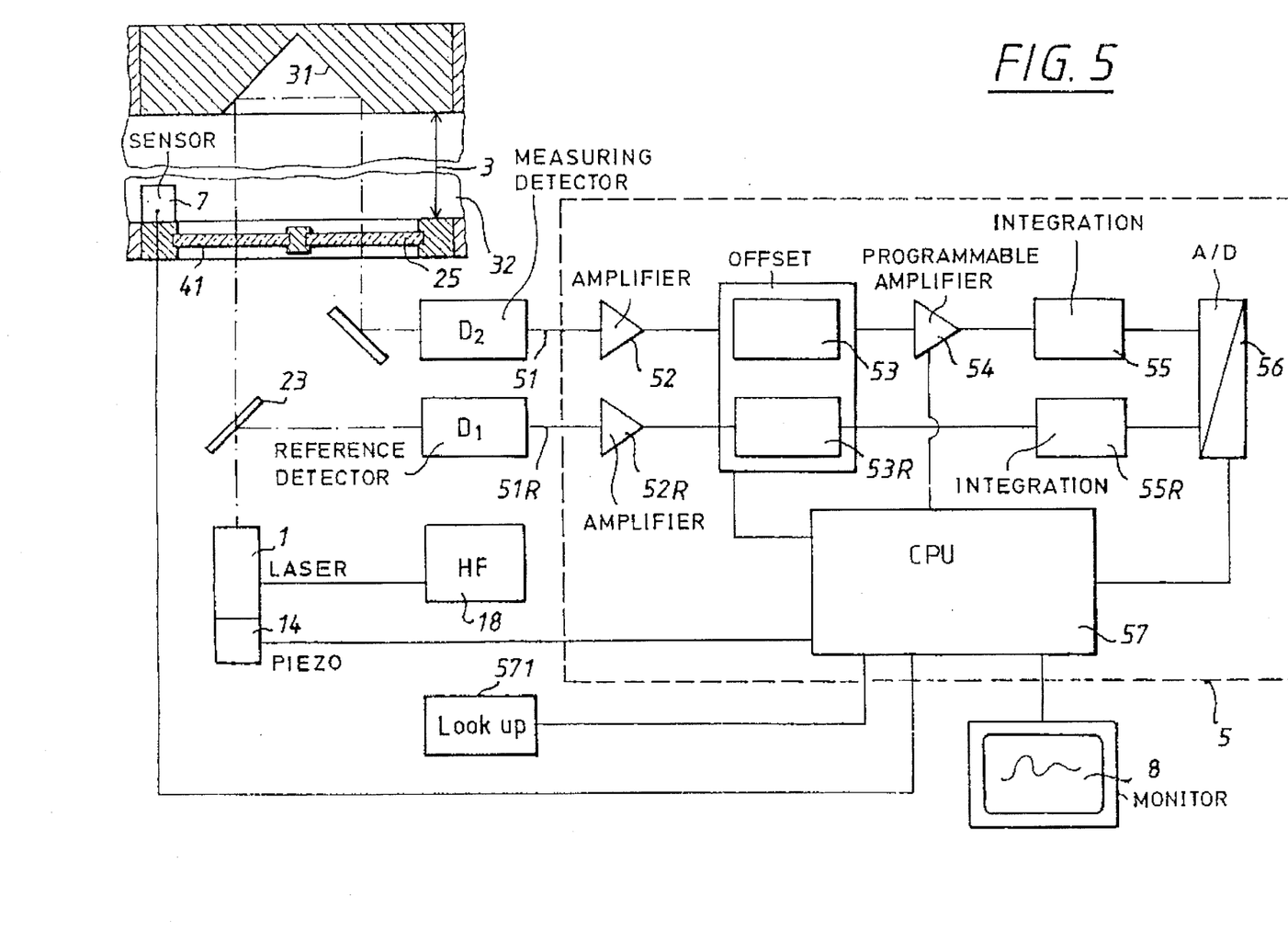

FIG. 5 shows a block circuit diagram of the evaluation apparatus 5 together with the key elements of the optical assembly and other circuit components. The same reference numerals are used in FIG. 5 to identify like components shown in FIGS. 1 and 3.

For both detectors (D1, D2), the evaluation apparatus includes respective alternating current couplings (51, 51R), amplifiers (52, 52R), offset controls (53, 53R) and integration units (55, 55R). A programmed adjustable amplifier circuit 54 is connected downstream of the measuring detector D2 directly forward of the integration unit 55. The adjustable amplifier 54 can have switching stages of multiples of 10, 100 and 1,000. For very high dynamics, the integration unit 55 and the downstream analog-to-digital converter 56 can be configured significantly simpler with respect to the detectors. The analog-to-digital converter 56 operates simultaneously for measurement and reference signals.

A programmable computer 57 evaluates the digitalized signals from the measuring beam path 3 at $\lambda_1$ and $\lambda_2$ and from reference detector D1 at $\lambda_1$ and $\lambda_2$ and generates concentration data. In this connection, reference may be made to U.S. Pat. No. 5,002,391 incorporated herein by reference.

A look-up table 571 for the ammonia absorption can be inputted or stored in memory externally. This look-up table 571, permits the data of the $NH_3$ concentration to be presented in any desired units. Data can also be considered which can be received from one or more sensors 7 in the flue-gas channel 32 and be directed to pressure, temperature or the like such as the concentration of carbon dioxide. In this way, the absolute concentration of the ammonia can be presented.

A monitor 8 is provided for outputting data.

The programmable computer 57 also controls the laser modulation via the piezoelectric positioning device 14 and the offset control (53, 53R) as well as the adjustable amplification circuit 54 and the time sequence of the integration (55, 55R) and can, as required, be programmed for further tasks and be connected via interfaces.

After passing through the measuring path 3, the laser radiation reaches the measuring detector D2 and a small portion of the radiation is guided via the beam splitter 23 directly to the reference detector D1. The detector signals from detectors (D1 and D2) are amplified in an AC-coupled manner because a DC offset signal occurs because of the needed bias current of the detectors. A fluctuation of the OV-line in dependence upon signal shape and signal amplitude results because of the alternating current coupling (51, 51R). The signals must be connected to the OV-level because the measuring/reference signals are evaluated by integration. This takes place in the offset control (53, 53R) by means of sample and hold. Thus, when the modulation signal passes through zero, a signal minimum is obtained. The difference of this value to 0 V is collected and added to the measuring signal for the next measuring cycle until a new measurement takes place at the next minimum. With this measure, a unipolar signal position of the measurement values is obtained so that an integration without sign change can be carried out (automatic offset control).

When taking the system into service, the operating point $U_{AP}$ of the laser 1 and the modulation voltage $U_{mod}$ are automatically determined. A spectrum analyzer for controlling the wavelength is superfluous because it is ensured that the laser 1 emits only at the two desired lines ($\lambda_1$, $\lambda_2$) because of the constructive design.

The following is carried out by the computer 57:

1) driving the piezoelectric positioning member 14;

2) recording the signature at the reference detector D1 and storing (minimum and maximum);

3) considering different powers of $\lambda_1$ and $\lambda_2$ over area ratio of $A_1/A_2$ (see FIG. 2);

4) determine operating point $U_{AP}$ and modulation swing $U_{mod}$.

The light attenuation or transmission is measured at the wavelength $\lambda_2$ and is uninfluenced by the ammonia. This light attenuation or transmission can be utilized to determine the flue gas density in the measurement volume 3. Precisely this is possible when the components of the exhaust-gas/flue-gas flow are known per se and the extinction coefficient of the flue gas is also known. The large wavelength in infrared which is used is advantageous because relatively large measurement lengths and flue gas densities are detected because of the reduced scattering. It is especially advantageous that this additional measurement is obtained only by corresponding programming of the computer 57.

The description of the invention with respect to a specific embodiment is not a limitation because numerous variations are possible. What is important is that the configuration of the invention makes it possible to operate without chopper or similar additional light modulators in the arrangement for detecting substances because the signature of the laser 1 provides for a reliable zero passthrough of the laser intensity. The sinusoidal modulation of the laser light can be processed with excellent correspondence with respect to waveform by the detectors D1 and D2 and the evaluation apparatus 5 without loss with the Fourier analysis or frequency response. This is in contrast to a square wave modulation. In this way, the integration of the signals and therefore the high utilization of the laser energy is possible for obtaining the signal. Square wave modulation with sample-and-hold-signal processing must, in contrast, leave a large portion of the laser pulse unused. A reference cell having a calibrated $NH_3$ content is likewise not continuously measured with its own detector. It is sufficient to introduce this on occasion for calibration purposes and to then utilize the measuring detector D2 provided.

It is understood that the foregoing description is that of the preferred embodiments of the invention and that various changes and modifications may be made thereto without departing from the spirit and scope of the invention as defined in the appended claims.

What is claimed is:

1. A gas laser comprising:

a waveguide in which a laser gas having a predetermined composition is present;

said waveguide defining an optical axis and having first and second ends;

an excitation source for exciting said laser gas to produce laser light;

an out-coupling mirror having a predetermined reflectivity and being mounted on said optical axis adjacent said first end;

a grating arranged on said optical axis adjacent said second end and having a number of grating lines and a predetermined resolution and an angular position relative to said optical axis;

said waveguide, said out-coupling mirror and said grating conjointly defining a resonator having a length (L) measured along said axis from said out-coupling mirror to said grating;

a modulator to modulate said length (L) sinusoidally from a first length within a first interval of length to a second length within a second interval of length measured along said axis; and, said grating, said angular position, said reflectivity, said length (L), said composition of said laser gas being selected so as to cause said gas laser to emit laser light along said optical axis at first and second wavelengths ($\lambda_1$, $\lambda_2$) when said length (L) is within first and second intervals, respectively, and to suppress emission of said laser light during transition between said intervals of length.

2. The gas laser of claim 1, said gas laser being a $CO_2$ laser and said grating being in a Littrow configuration.

3. The gas laser of claim 2, said gas laser containing isotope $^{13}C$ and said first wavelength $\lambda_1$ being 10.800 μm for line R (16) and said second wavelength $\lambda_2$ being 10.784 μm for line R (18).

4. The gas laser of claim 1, said resonator length (L) being determined pursuant to:

$$L = (n + \tfrac{1}{2}) \cdot L_0$$

wherein:

n is an integer $L_0$ is the smallest length at which resonance occurs for both of said wavelengths ($\lambda_1$, $\lambda_2$).

5. The gas laser of claim 1, said modulator comprising a piezoelectric actuating element for linearly displacing said grating along said axis between said first and second intervals.

6. An arrangement for detecting a substance present in a measuring path, the arrangement comprising:

a gas laser including: a waveguide in which a laser gas having a predetermined composition is present; said waveguide defining an optical axis and having first and second ends; an excitation source for exciting said laser gas to produce laser light; an out-coupling mirror having a predetermined reflectivity and being mounted on said optical axis adjacent said first end; a grating arranged on said optical axis adjacent said second end and having a number of grating lines and a predetermined resolution and an angular position relative to said optical axis; said waveguide, said out-coupling mirror and said grating conjointly defining a resonator having a length (L) measured along said axis from said out-coupling mirror to said grating; a modulator to modulate said length (L) sinusoidally from a first length within a first interval of length to a second length within a second interval of length measured along said axis; said grating structure, said angular position, said reflectivity, said length (L), said composition of said laser gas being selected so as to cause said gas laser to emit laser light along said optical axis at first and second wavelengths ($\lambda_1$, $\lambda_2$) when said length (L) is within first and second intervals, respectively, and to suppress emission of said laser light during transition between said intervals of length; and, an evaluation device for computing a ratio of light absorption by said substance for said two wavelengths ($\lambda_1$, $\lambda_2$) to determine therefrom the concentration of said substance.

7. The arrangement of claim 6, further comprising:

a beam splitter for splitting said laser light beam into a reference beam defining a reference beam path and a work beam defining a work beam path;

a reference detector mounted in said reference beam path for supplying a reference signal indicative of said reference beam;

a transmission optic mounted in said work beam path for transmitting said work beam into said measuring path where some of the light of each of said two wavelengths ($\lambda_1$, $\lambda_2$) is absorbed;

a measuring detector mounted downstream of said measuring path for receiving said work beam and for supplying a measurement signal indicative of said work beam; and, said evaluation device being connected to said detectors for receiving said signals.

8. The arrangement of claim 7, said measuring path being open and said arrangement further comprising a reflector for folding said work beam thereby permitting said work beam to pass through said measuring path at least twice.

9. The arrangement of claim 7, further comprising optics for directing said work beam along a reference path; a cell for holding a known concentration of said substance; and, said cell being mounted in said reference beam path for calibration purposes.

10. The arrangement of claim 6, wherein said substance is ammonia flowing through a smoke gas channel; and, said measuring path being in said smoke gas channel.

11. The arrangement of claim 7, further comprising an apparatus for adjusting the power of said work beam to adapt said power to the concentration of said substance which is present in said measuring path.

12. The arrangement of claim 7, wherein said measuring detector is an MCT detector.

13. The arrangement of claim 7, said evaluation device including alternating-current connecting circuits for connecting corresponding ones of said detectors to said evaluation device; an amplifier being connected to said alternating-current connecting circuits; an integrator connected to said amplifier; an analog-to-digital converter connected to said integrator; and, a programmable computer connected to said analog-to-digital converter.

14. The arrangement of claim 13, wherein said gas laser emits said laser light at one of said two wavelengths ($\lambda_1, \lambda_2$) over repeated time intervals; said integrator including a circuit to integrate said measurement signal of said measuring detector over most part ($t_1-t_2$) of each of said time intervals.

15. The arrangement of claim 13, said amplifier having an amplification factor; and said evaluation device further including a circuit for automatically adjusting said amplification factor in dependence upon said measurement signal.

16. The arrangement of claim 6, wherein said arrangement is exclusively modulated by said modulator.

17. The arrangement of claim 6, wherein said reference path contains only two detectors.

18. The arrangement of claim 6, wherein said substance includes ammonia and flue gas and the laser light of said second wavelength ($\lambda_2$) is not absorbed by ammonia; and, wherein said evaluation device includes a circuit for obtaining a measurement value for the density of said flue gas from the absorption data obtained from the laser light of said second wavelength.

* * * * *

UNITED STATES PATENT AND TRADEMARK OFFICE
CERTIFICATE OF CORRECTION

PATENT NO. : 5,544,186

DATED : August 6, 1996

INVENTOR(S) : Ralf-Roland Sauer, Wolfgang Rupp and Alexander Hinz

It is certified that error appears in the above-identified patent and that said Letters Patent is hereby corrected as shown below:

In column 4, line 32: delete "(68.5.3.63 mm)." and substitute -- (68.5 · 3.63 mm). -- therefor.

In column 4, line 35: delete "27" and substitute -- 2.7 -- therefor.

In column 4, line 45: delete "N" and substitute -- $N_2$ -- therefor.

In column 4, line 51: delete "$\lambda_1$" (second occurrence) and substitute -- $\lambda_2$ -- therefor.

In column 4, line 54: delete "$P_{mod}$" and substitute -- $P_{out}$ -- therefor.

In column 5, line 41: delete "point" and substitute -- points -- therefor.

Signed and Sealed this

First Day of April, 1997

Attest:

*Attesting Officer*

BRUCE LEHMAN

*Commissioner of Patents and Trademarks*